(12) United States Patent
Filler

(10) Patent No.: US 7,059,368 B2
(45) Date of Patent: Jun. 13, 2006

(54) NEEDLE GUIDE

(75) Inventor: Aaron G. Filler, Santa Monica, CA (US)

(73) Assignee: Point Guard Medical, Incorporated, Encino, CA (US)

( * ) Notice: Subject to any disclaimer, the term of this patent is extended or adjusted under 35 U.S.C. 154(b) by 103 days.

(21) Appl. No.: 10/982,713

(22) Filed: Nov. 4, 2004

(65) Prior Publication Data

US 2005/0187533 A1   Aug. 25, 2005

Related U.S. Application Data

(60) Provisional application No. 60/546,664, filed on Feb. 20, 2004.

(51) Int. Cl.
*B65B 1/04* (2006.01)
(52) U.S. Cl. .................. 141/329; 141/27; 604/416
(58) Field of Classification Search ........... 141/329, 141/330, 21–27; 604/416
See application file for complete search history.

(56) References Cited

U.S. PATENT DOCUMENTS 4,982,769 A * 1/1991 Fournier et al. ............ 141/98
5,088,996 A * 2/1992 Kopfer et al. .............. 604/415
5,827,262 A * 10/1998 Neftel et al. ............... 604/414

* cited by examiner

*Primary Examiner*—Steven O. Douglas
(74) *Attorney, Agent, or Firm*—David A. Farah; Sheldon & Mark PC

(57) ABSTRACT

A needle guide for decreasing the incidence of needle injury to an operator who is accessing the interior of a container, such as a medical fluid container, by an accessing device, such as a syringe with a needle attached to the distal end of the syringe. A device for decreasing the incidence of needle injury to an operator who is accessing the interior of the container by an accessing device, such as a syringe with a needle attached to the distal end of the syringe, the device comprising a container, such as a medical fluid container, with an integrated needle guide. A method of decreasing the incidence of needle injury to an operator who is accessing the interior of a container, such as a medical fluid container, by an accessing device, such as a syringe with a needle attached to the distal end of the syringe, the method comprising providing a needle guide according to the present invention, or providing a device comprising a container with an integrated needle guide according to the present invention.

57 Claims, 10 Drawing Sheets

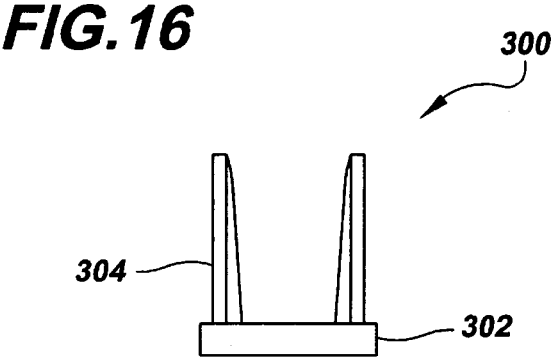
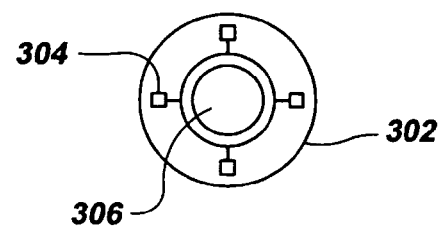
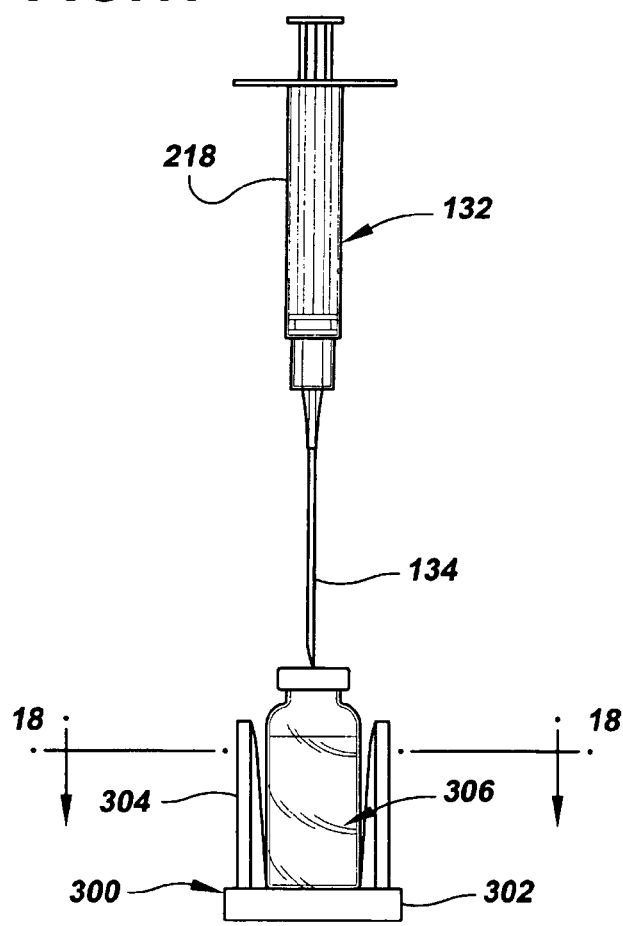

NEEDLE GUIDE

CROSS-REFERENCE TO RELATED APPLICATIONS

The present application claims the benefit of U.S. provisional patent application 60/546,664, titled "Needle Guide Device," filed Feb. 20, 2004, the contents of which are incorporated in this disclosure by reference in their entirety.

BACKGROUND

Many types of fluids used in the hospital or clinical setting are stored in specialized containers prior to use. One common type of medical container has a clear distal storage portion made of, for example, glass, and a proximal portion comprising a membrane made of, for example, rubber. An operator accesses the interior of the distal storage portion in this type of container using an accessing device having a needle at the distal end, by inserting the needle through the membrane into the distal storage portion, and then withdrawing or adding fluid to the container. Another common type of specialized container is a "snap-open" container, which has a clear distal storage portion and a proximal portion generally made of the same material, such as glass, with a scored junction between the distal storage portion and the proximal portion. An operator accesses the interior of the distal storage portion in this type of container by breaking the container at the junction, thereby separating the distal storage portion from the proximal portion, and then inserting the needle on the distal end of an accessing device into the distal storage portion to withdraw or add fluid.

Accessing fluid in either of these types of container carries a significant risk of a needle injury to the operator because, when the operator inserts a needle into the distal storage portion of the container using one hand, the operator directs the needle toward the operator's opposing hand or to another person's hand that is holding the container. Failure to direct the needle properly will often result in a needle injury to the hand holding the container. Therefore, there is a need for a device and method that decreases the risk of a needle injury when an operator inserts a needle into a container.

SUMMARY

According to one embodiment of the present invention, there is provided a needle guide for decreasing the incidence of needle injury to an operator who is accessing the interior of a container, such as a medical fluid container, by an accessing device, such as a syringe with a needle attached to the distal end of the syringe. The needle guide comprises a proximal portion comprising a proximal end that is at least partly open and comprises a distal end, and a distal portion connected to the proximal portion. The distal portion comprises a proximal end and comprises a distal end that is at least partly open. The proximal portion comprises an inner surface that tapers from the proximal end of the proximal portion to the distal end of the proximal portion. The distal portion comprises an inner surface that is continuous with the inner surface of the proximal portion though an opening. The distal portion is configured such that the inner surface of the distal portion fits snugly over part or all of the container to be accessed.

In one embodiment, the proximal portion has a substantially conical shape with the larger end proximally and the narrow end distally. In another embodiment, the needle guide further comprises one or more than one seal, sealing the proximal end of the proximal portion and sealing the distal end of the distal portion of the needle guide to maintain sterility of the inner surface of the proximal portion and the inner surface of the distal portion of the needle guide prior to use. In one embodiment, the seal is a metal foil removably attached to the lip of the proximal portion by an adhesive. In another embodiment, the seal is a wrapping covering the entire needle guide. In a preferred embodiment, the seal is resealable. In a preferred embodiment, the seal comprises a first layer and a second layer, and further comprises a sterilizing pad between the first layer and the second layer. In a preferred embodiment, the proximal portion and the distal portion of the needle guide are configured to be separable from one another by the operator. In one embodiment, the distal end of the proximal portion comprises a mechanism that mates with a companion mechanism on the proximal end of the distal portion device.

According to another embodiment of the present invention, there is provided a device for decreasing the incidence of needle injury to an operator who is accessing the interior of the container by an accessing device, such as a syringe with a needle attached to the distal end of the syringe. The device comprises a container comprising a proximal portion and a distal storage portion. The device further comprises a needle guide comprising a proximal portion with a proximal end and a distal end, and the needle guide further comprises a distal portion that is integrally attached to the proximal portion of container. The proximal portion of the needle guide tapers from the proximal end to the distal end.

In one embodiment, the proximal portion of the needle guide has a substantially conical shape with the larger end proximally and the narrow end distally. In another embodiment, the proximal portion of the needle guide has an inner surface, and the device further comprises a seal, sealing the proximal end of the proximal portion of the needle guide to maintain sterility of the inner surface of the proximal portion prior to use. In a preferred embodiment, the seal is a metal foil removably attached to the lip of the proximal portion of the needle guide by an adhesive. In another preferred embodiment, the seal is a wrapping covering the entire device. In a preferred embodiment, the seal is resealable.

According to another embodiment of the present invention, there is provided a method of decreasing the incidence of needle injury to an operator who is accessing the interior of a container, such as a medical fluid container, by an accessing device, such as a syringe with a needle attached to the distal end of the syringe. The method comprises, first, providing a container comprising a proximal portion and comprising a distal storage portion whose interior is to be accessed, and providing a needle guide according to the present invention. Then, the distal portion of the needle guide is inserted over the proximal portion of the container until the distal end of the proximal portion of the needle guide contacts or comes in close proximity to the proximal portion of the container. Next, an accessing device comprising a needle at the distal end is provided. Then, the needle is inserted through the proximal portion of the needle guide and through the proximal portion of the container, thereby accessing the distal storage portion of the container.

In one embodiment, the proximal portion of the container comprises a seal, and the method further comprises removing the seal. In another embodiment, the distal end of the distal portion of the needle guide comprises a seal, and the method further comprises removing the seal. In another embodiment, the proximal end of the proximal portion of the needle guide comprises a seal, and the method further comprises removing the seal. In another embodiment, the method further comprises resealing the proximal end of the proximal portion of the needle guide.

In one embodiment, the method further comprises withdrawing material from the container through the needle or introducing material into the container from the accessing device. In another embodiment, the method further comprises withdrawing the needle from the proximal portion of the container, and from the needle guide. In a preferred embodiment, the container is a "snap-open" type of medical fluid container comprising a breakable junction between the proximal portion and the distal storage portion, and the method further comprises separating the proximal portion of the container from the distal storage portion of the container by breaking the container at the junction. In a preferred embodiment, the container is a "snap-open" type of medical fluid container comprising a breakable junction between the proximal portion and the distal storage portion, the proximal portion and the distal portion of the needle guide are configured to be separable from one another by the operator, and the method further comprises inserting distal portion of needle guide over the distal storage portion of the container before separating the proximal portion from the distal storage portion by breaking the container at the junction, separating the distal storage portion of the container from the proximal portion by breaking the container at the junction, removing the distal storage portion, and then joining the proximal portion of the needle guide to the distal portion of the needle guide.

According to another embodiment of the present invention, there is provided a method of decreasing the incidence of needle injury to an operator who is accessing the interior of a container, such as a medical fluid container, by an accessing device, such as a syringe with a needle attached to the distal end of the syringe. The method comprises, first, providing a device according to the present invention. Next, an accessing device comprising a needle at the distal end is provided. Then, the needle is inserted through the proximal portion of the needle guide and through the proximal portion of the container, thereby accessing the distal storage portion of the container. In one embodiment, the proximal end of the proximal portion of the needle guide comprises a seal, and the method further comprises removing the seal. In another embodiment, the method further comprises resealing the proximal end of the proximal portion of the needle guide. In another embodiment, the method further comprises withdrawing material from the container through the needle or introducing material into the container from the accessing device. In another embodiment, the method further comprises withdrawing the needle from the proximal portion of the container and from the needle guide.

According to another embodiment of the present invention, there is provided a device for decreasing the incidence of needle injury to an operator who is accessing the interior of the container by an accessing device, such as a syringe with a needle attached to the distal end of the syringe. The device comprises a base comprising a center and a periphery, and a proximal side and a distal side. The device further comprises a plurality of supports attached to the base extending generally perpendicular to the base and oriented circumferentially around the periphery of the proximal side of the base. The base and supports are configured generally to retain the container, and the base is magnetic and of sufficient strength and configuration to attract a needle approaching the base from proximal to the supports toward the center of the base.

According to another embodiment of the present invention, there is provided a method of decreasing the incidence of needle injury to an operator who is accessing the interior of a container comprising a proximal portion and a distal storage portion to be accessed, by an accessing device comprising a needle at the distal end. The method comprises, first, providing a device according to the present invention. Next, the container is placed between the supports. Then, the accessing device is provided. Next, the needle is inserted through the proximal portion of the container, thereby accessing the distal storage portion of the container. In one embodiment, the method further comprises withdrawing material from the container through the needle or introducing material into the container from the accessing device. In another embodiment, the method further comprises withdrawing the needle from the proximal portion of the container.

According to another embodiment of the present invention, there is provided a device for decreasing the incidence of needle injury to an operator who is accessing the interior of the container by an accessing device, such as a syringe with a needle attached to the distal end of the syringe. The device comprises a proximal actuating portion and a distal retaining portion connected to the proximal actuating portion. The proximal actuating portion is configured to reversibly open and close the distal retaining portion. The distal retaining portion comprises a magnet of sufficient strength and configuration to attract a needle approaching the distal retaining portion and to guide the needle toward the center of the distal retaining portion. The distal retaining portion is configured to grasp the container. In one embodiment, the distal retaining portion comprises a plurality of arms. In one embodiment, the arms form an incomplete circular enclosure. In another embodiment, the arms form a cylinder.

According to another embodiment of the present invention, there is provided a method of decreasing the incidence of needle injury to an operator who is accessing the interior of a container comprising a proximal portion and a distal storage portion to be accessed, by an accessing device comprising a needle at the distal end. The method comprises, first, providing a device according to the present invention. Next, the container to be accessed is provided. Then, the distal retaining portion is actuated to grasp the proximal portion of the container with the distal retaining portion. Next, the accessing device is provided. Then, the needle is inserted through the proximal portion of the container, thereby accessing the distal storage portion of the container. In one embodiment, the method further comprises withdrawing material from the container through the needle or introducing material into the container from the accessing device. In another embodiment, the method further comprises withdrawing the needle from the proximal portion of the container. In another embodiment, the method further comprises sterilizing the distal retaining portion prior to actuating the distal retaining portion.

According to another embodiment of the present invention, there is provided a device for decreasing the incidence of needle injury to an operator who is accessing the interior of the container by an accessing device. The device comprises a proximal portion comprising a center and a periphery, and a distal portion attached to the proximal portion, and comprising a center and a periphery. The proximal portion comprises magnetic particles in a configuration more dense around the periphery and less dense in the center, and the distal portion is configured to fit snugly into the proximal opening of the container. In one embodiment, the distal portion comprises magnetic particles in a configuration more dense around the periphery and less dense in the center. In another embodiment, the magnetic particles are embedded directly into the proximal portion. In another embodiment, the proximal portion comprises a washer with the magnetic particles embedded into the washer, and where the washer is attached to or embedded directly in the proximal portion.

According to another embodiment of the present invention, there is provided a method of decreasing the incidence of needle injury to an operator who is accessing the interior of a container comprising a proximal portion and a distal storage portion to be accessed, by an accessing device comprising a needle at the distal end. The method comprises, first, providing a device according to the present invention. Next, the container to be accessed is provided. Then, the distal portion of the device is introduced into the proximal portion of the container, thereby substantially sealing the proximal portion of the container. Next, the accessing device is provided. Then, the needle is inserted through the proximal portion of the device and into the container. In one embodiment, the method further comprises withdrawing material from the container through the needle or introducing material into the container from the accessing device. In another embodiment, the method further comprises withdrawing the needle from the proximal portion of the container.

According to another embodiment of the present invention, there is provided a device for decreasing the incidence of needle injury to an operator who is accessing the interior of the container by an accessing device. The device comprises a proximal portion and a distal storage portion attached to the proximal portion, and a needle guide comprising a center and a periphery. The needle guide is integrally attached to the proximal portion and seals the proximal portion of the device. The needle guide comprises magnetic particles in a configuration more dense around the periphery and less dense in the center. In one embodiment, the device further comprises a seal covering the needle guide to maintain sterility of the needle guide before use.

According to another embodiment of the present invention, there is provided a method of decreasing the incidence of needle injury to an operator who is accessing the interior of a device comprising a proximal portion and a distal storage portion to be accessed, by an accessing device comprising a needle at the distal end. The method comprises, first, providing a device according to the present invention. Next, the accessing device is provided. Then, the needle is inserted through the needle guide of the device, thereby accessing the distal storage portion. In one embodiment, the device provided further comprises a seal covering the needle guide to maintain sterility of the needle guide before use, and the method further comprises removing the seal. In another embodiment, the method further comprises withdrawing material from the device through the needle or introducing material into the device from the accessing device. In another embodiment, the method further comprises withdrawing the needle from the device.

FIGURES

These and other features, aspects and advantages of the present invention will become better understood with regard to the following description, appended claims, and accompanying figures where:

FIG. 16 is a lateral perspective view of one embodiment of the magnetic device according to the present invention;

FIG. 17 is another lateral perspective view of the embodiment of the magnetic device shown in FIG. 16 being used to guide a needle from an accessing device into a container retained in the device;

FIG. 18 is a top perspective view of the embodiment shown in FIG. 17 taken along line 18—18 (FIG. 18);

DESCRIPTION

According to one embodiment of the present invention, there is provided a needle guide for decreasing the incidence of needle injury to an operator who is accessing the interior of a container, such as a medical fluid container, by an accessing device, such as a syringe with a needle attached to the distal end of the syringe. According to another embodiment of the present invention, there is provided a device for decreasing the incidence of needle injury to an operator who is accessing the interior of the container by an accessing device, such as a syringe with a needle attached to the distal end of the syringe, the device comprising a container, such as a medical fluid container, with an integrated needle guide. According to another embodiment of the present invention, there is provided a method of decreasing the incidence of needle injury to an operator who is accessing the interior of a container, such as a medical fluid container, by an accessing device, such as a syringe with a needle attached to the distal end of the syringe. The method comprises providing a needle guide according to the present invention, or providing a device comprising a container with an integrated needle guide according to the present invention. The needle guides, devices and methods of the present invention will now be disclosed in greater detail.

As used in this disclosure, the term "comprise" and variations of the term, such as "comprising" and "comprises," are not intended to exclude other additives, components, integers or steps.

As used in this disclosure, two components are "integrated" if they are not intended or configured to be separated by the end user.

As used in this disclosure, the term "operator" should be understood to include both the person holding the accessing device, as well as another person holding the container if two persons jointly access the interior of the container.

All dimensions specified in this disclosure are by way of example only and are not intended to be limiting. Further, the proportions shown in these Figures are not necessarily to scale. As will be understood by those with skill in the art with reference to this disclosure, the actual dimensions of any device or part of a device disclosed in this disclosure will be determined by its intended use.

All method steps shown in the Figures are not intended to be limiting nor are they intended to indicate that each step depicted is essential to the method or that the order of the steps depicted are essential, but instead are exemplary steps only.

Figure 1:
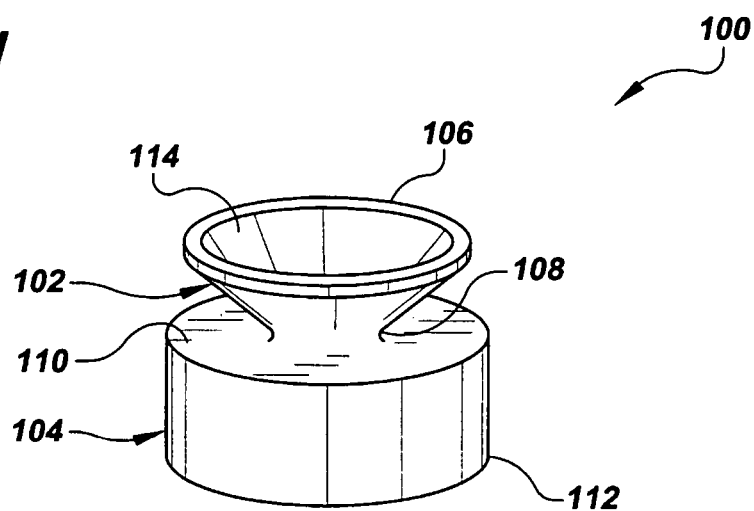
FIG. 1 is a lateral perspective view of a needle guide according to one embodiment of the present invention.
Figure 2:
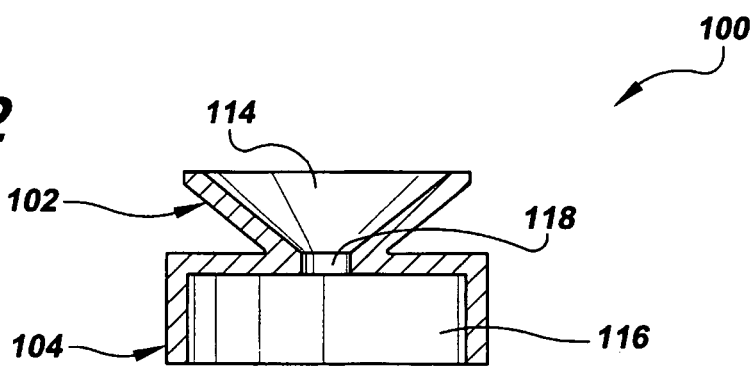
FIG. 2 is a cutaway, lateral perspective view of the needle guide shown in FIG. 1.
Figure 3:
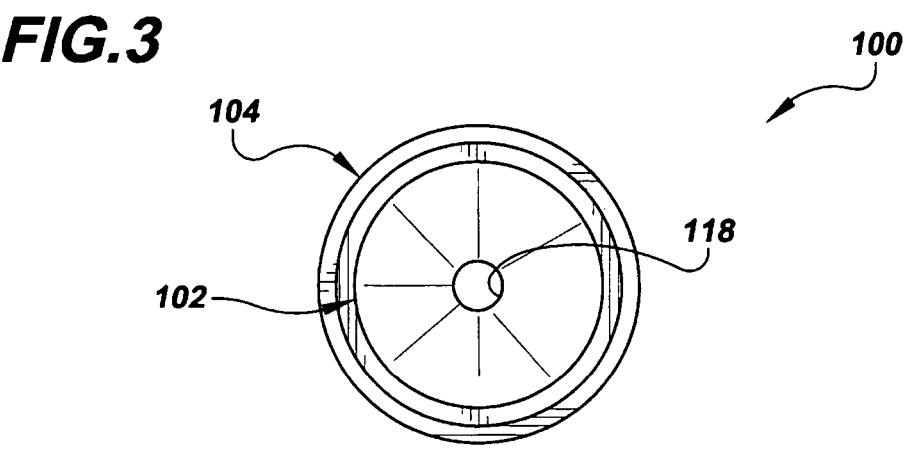
FIG. 3 is a top perspective view of the needle guide shown in FIG. 1.
Figure 4:
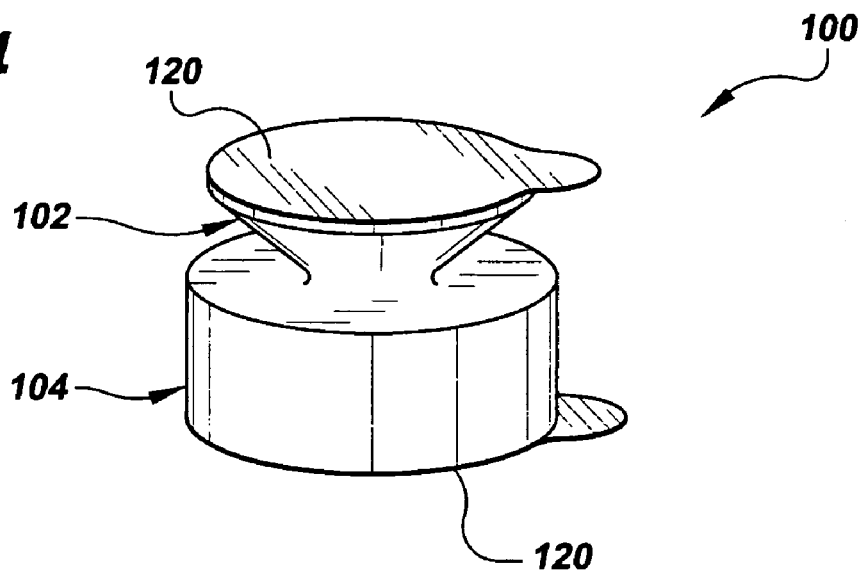
FIG. 4 is a lateral perspective view of the needle guide shown in FIG. 1 with the proximal opening and the distal opening sealed to maintain sterility of the inner surfaces of the needle guide prior to use.

In one embodiment, the present invention is a needle guide for decreasing the incidence of needle injury to an operator who is accessing the interior of a container, such as a medical fluid container, by an accessing device, such as a syringe with a needle attached to the distal end of the syringe. Referring now to FIG. 1 through FIG. 4, there are shown, respectively, a lateral perspective view of a needle guide according to one embodiment of the present invention (FIG. 1); a cutaway, lateral perspective view of the needle guide shown in FIG. 1 (FIG. 2); a top perspective view of the needle guide shown in FIG. 1 (FIG. 3); and a lateral perspective view of the needle guide shown in FIG. 1 with the proximal opening and the distal opening sealed to maintain sterility of the inner surfaces of the needle guide prior to use (FIG. 4). As can be seen, the needle guide 100 comprises a proximal portion 102 connected to a distal portion 104. The proximal portion 102 has a proximal end 106 that is at least partly open and a distal end 108. The distal portion 104 has a proximal end 110 and has a distal end 112 that is at least partly open. The inner surface 114 of the proximal portion 102 of the needle guide 100 tapers from the proximal end 106 of the proximal portion 102 to the distal end 108 of the proximal portion 102, and is continuous with the inner surface 116 of the distal portion 104 through an opening 118. The distal portion 104 is configured such that the inner surface 116 of the distal portion 104 fits snugly over part or all of the container to be accessed.

In a preferred embodiment, as shown in FIG. 1 through FIG. 4, the proximal portion 102 has a substantially conical shape with the larger end proximally and the narrow end distally, and the distal portion 104 has a substantially cylindrical shape configured to fit over the proximal end of one common type of medical fluid container. However, as will be understood by those with skill in the art with reference to this disclosure, the proximal portion 102 and the distal portion 104 can have other shapes as appropriate for the purposes disclosed in this disclosure. For example, the proximal portion 102 can be funnel-shaped or bowl-shaped rather than substantially conical, and the distal portion 104 can be configured to fit over injection ports on intravenous solution bags and on intravenous tubing sets, as well as any other suitable tubing, containers, filtering devices, culture vials, vats, incubators, chromatography columns, centrifugal separators, and multiple well plates, as will be understood by those with skill in the art, with reference to this disclosure.

In another preferred embodiment, the distal portion 104 of the needle guide 100 is substantially clear. In another preferred embodiment, the needle guide 100 further comprises one or more than one seal 120, sealing the proximal end 106 of the proximal portion 102 and sealing the distal end 112 of the distal portion 104 of the needle guide 100 to maintain sterility of the inner surface 114 of the proximal portion 102 and the inner surface 116 of the distal portion 104 of the needle guide 100 prior to use. Referring again to FIG. 4, there is shown such a seal 120 over the proximal opening 122. In a preferred embodiment, the seal 120 is a metal foil removably attached to the lip of the proximal portion 102 by an adhesive. A similar seal would be used to seal the lip of distal portion 104. In a preferred embodiment, the seal 120 is a wrapping covering the entire needle guide 100. The seal 120 can also be a screw-on type made to mate with matching threads in the proximal end 106 of the proximal portion 102, or can be a hinged, snap-on type that can be repeatedly opened and closed, thereby allowing the needle guide 100 to be resealable. The needle guide 100 can be made of any suitable material that can be sterilized, as will be appreciated by one of ordinary skill in the art with reference to this disclosure. For example, in a preferred embodiment, the needle guide 100 comprises one or more than one material selected from the group consisting of a plastic polymer, a low-density polyethylene and a metal.

Figure 5:
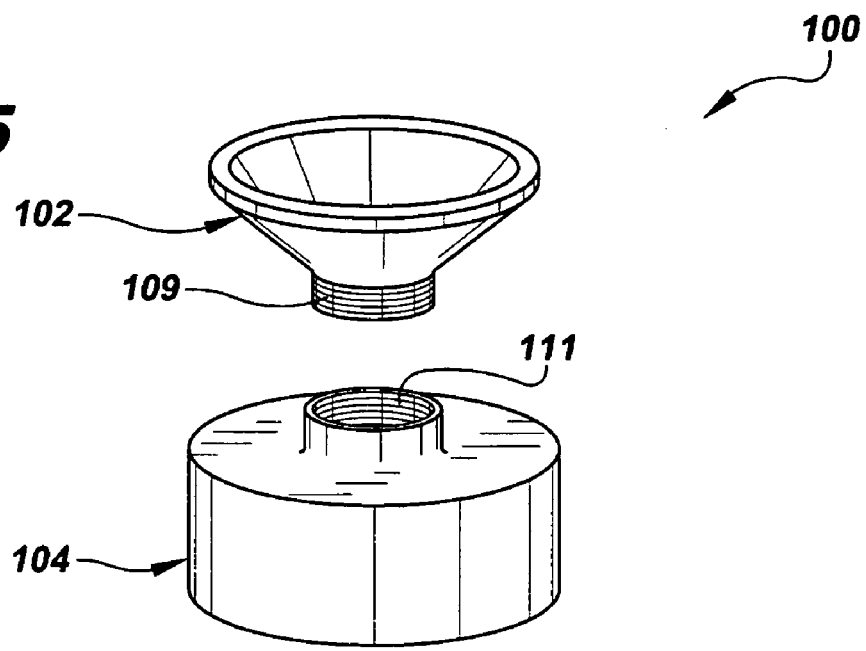
FIG. 5 is a lateral perspective view of an embodiment of the needle guide shown in FIG. 1 through FIG. 4, where the proximal portion and the distal portion are separable and separated.

In another preferred embodiment, the proximal portion 102 and the distal portion 104 of the needle guide 100 are configured to be separable from one another by the operator. Referring now to FIG. 5, there is shown a lateral perspective view of an embodiment of the needle guide 100 shown in FIG. 1 through FIG. 4, where the proximal portion 102 and the distal portion 104 are separable and separated. As can be seen, the distal end 108 of the proximal portion 102 comprises a mechanism 109 that mates with a companion mechanism 111 on the proximal end 110 of the distal portion 104 according to this embodiment of the present invention. Though depicted as interlocking screw-type mechanisms, any other suitable mechanism can also be utilized as will be understood by those with skill in the art with reference to this disclosure.

By way of example only, when configured to be used with a conventional medical fluid container, the proximal portion 102 of the needle guide 100 can have an axial length of between about 0.5 cm and 2.0 cm, and a maximal width of between about 1 cm and 3 cm. In a preferred embodiment, the proximal portion 102 of the needle guide 100 has an axial length of about 1 cm and a maximal width of about 2 cm. As will be understood by those with skill in the art with reference to this disclosure, though the needle guide 100 is shown having a distal portion 104 with a relatively short axial length compared to the axial length of the proximal portion 102, the distal portion 104 can have a substantially longer axial length to fit over, not only the proximal portion of a container, but also part, most of, or all of the distal portion of the container.

Figure 6:
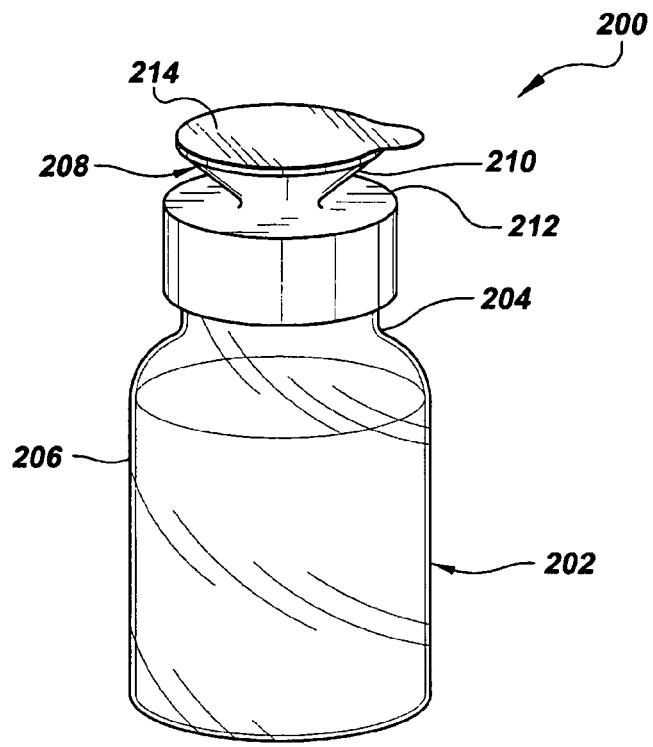
FIG. 6 is a lateral perspective view of a device according to the present invention for decreasing the incidence of needle injury to an operator who is accessing the interior of the container by an accessing device, such as a syringe with a needle attached to the distal end of the syringe.
Figure 7:
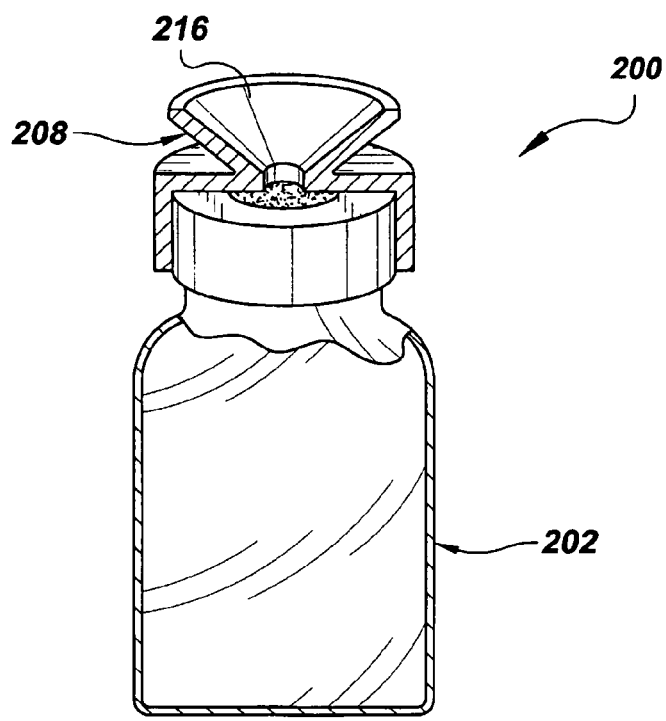
FIG. 7 is a cutaway, lateral perspective view of the device shown in FIG. 6.
Figure 8:
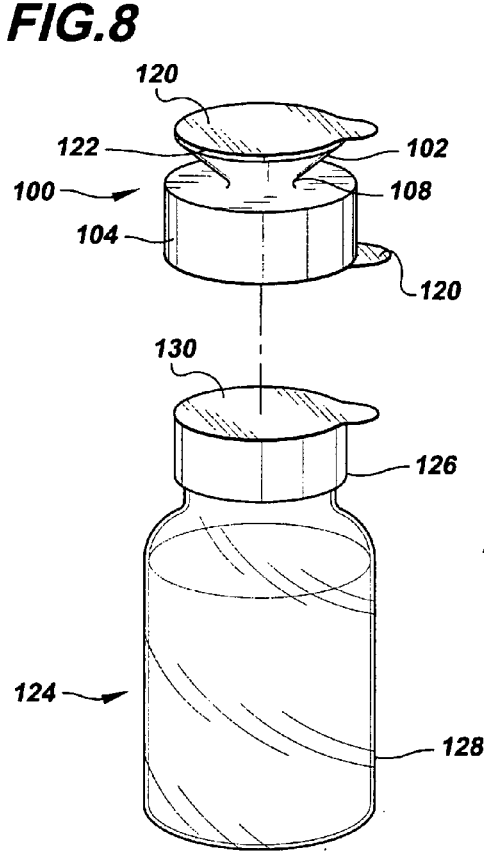
FIG. 8 through FIG. 12 show various steps of some embodiments of a method according to the present invention of decreasing the incidence of needle injury to an operator who is accessing the interior of a container, such as a medical fluid container, by an accessing device, such as a syringe with a needle attached to the distal end of the syringe.
Figure 9:
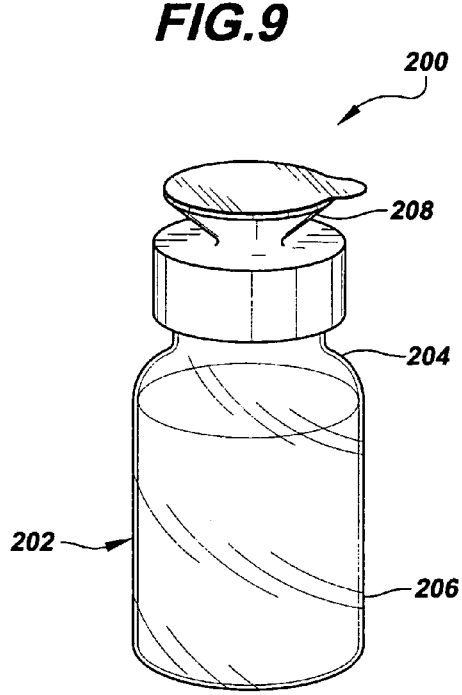

According to another embodiment of the present invention, there is provided a device for decreasing the incidence of needle injury to an operator who is accessing the interior of the container by an accessing device, such as a syringe with a needle attached to the distal end of the syringe. The device comprises a container, such as a medical fluid container, with an integrated needle guide. Referring now to FIG. 6 and FIG. 7, there are shown, respectively, a lateral perspective view of one embodiment of a device according to the present invention (FIG. 6); and a cutaway, lateral perspective view of the device shown in FIG. 6 (FIG. 7). As can be seen, the device 200 comprises a container 202 comprising a proximal portion 204 and a distal storage portion 206. The container 200 further comprises a needle guide 208, integrally attached to the proximal portion 204 of container 200. In a preferred embodiment, the form and attributes of the needle guide 208 corresponds generally to the form and attributes of the needle guide 100 according to the present invention as will be understood by those with skill in the art with reference to this disclosure, except as noted in this disclosure. As can be seen, the needle guide 208 comprises a proximal portion 210 and a distal portion 212. The distal portion 212 of the needle guide 208 is integrally attached to the proximal portion 204 of the container 202, such as by an adhesive joining the inner surface of the distal portion 212 of the needle guide 208 to the proximal portion 204 of the container 202. Alternately, the distal portion 212 of the needle guide 208 can be integrally manufactured as part of the proximal portion 204 of the container 202. As with the needle guide 100 disclosed above, a seal 214 is preferably used to seal the proximal opening 216 of the needle guide 208 prior to use to maintain sterility of the inner surface of the needle guide 208 before use. In one embodiment, the seal 214 covers only the proximal opening 216 of the needle guide 208. In another embodiment, the seal 214 covers the entire device 200. In another embodiment, the seal 214 is resealable.

In another embodiment, the present invention is a method of decreasing the incidence of needle injury to an operator who is accessing the interior of a container, such as a medical fluid container, by an accessing device, such as a syringe with a needle attached to the distal end of the syringe. Referring now to FIG. 1 through FIG. 12, there are shown various devices used in the method, and various steps of some embodiments of the method according to the present invention.

Figure 10:
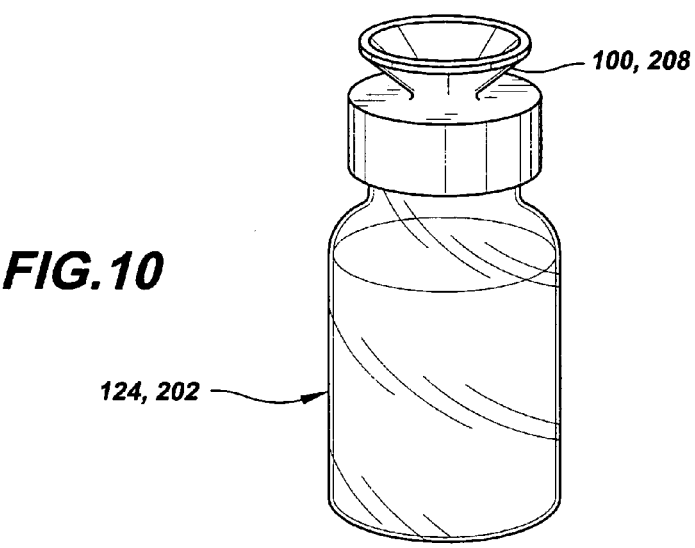
Figure 11:
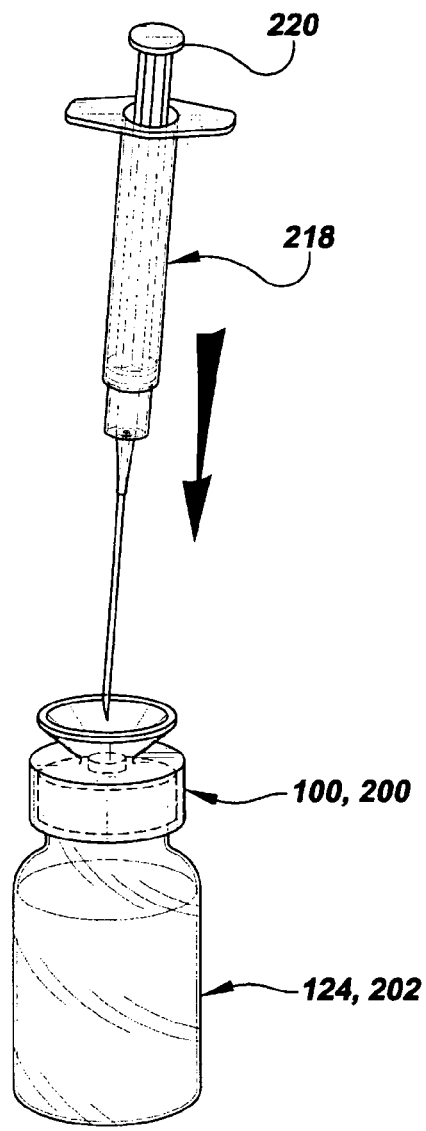
Figure 12:
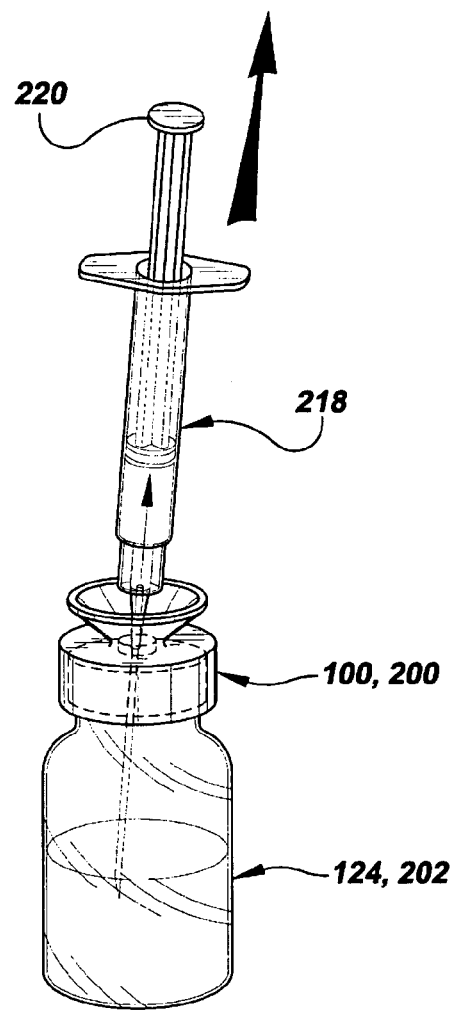

The method comprises, first, providing a container whose interior is to be accessed, and providing a needle guide. In one embodiment, the container 124 is a medical fluid container, and the needle guide is a needle guide according to the present invention, such as a needle guide 100 as shown in FIG. 1 through FIG. 4, where the container 124 and needle guide are not integral. In another embodiment, the container and needle guide are integrated, such as the device 200 according to the present invention shown in FIG. 6 and FIG. 7. The container 124, 202 comprises a proximal portion 126, 204 and a distal storage portion 128, 206. With respect to the embodiment of the method where the container 124 and needle guide 100 that are not integrated, if the proximal portion 126 of the container 124 comprises a seal 130 present to maintain sterility, the seal 130 is removed. If the distal portion 104 of the needle guide 100 comprises a seal 120 covering the distal end 112 of the distal portion 104, the seal 120 is removed. Next, as shown in FIG. 10, the distal portion 104 of the needle guide 100 is inserted over the proximal portion 126 of the container 124 until that the distal end 108 of the proximal portion 102 of the needle guide 100 contacts or comes in close proximity to the proximal portion 126 of the container 124. With respect now to both embodiments, one where the container 124 and needle guide 100 are not integrated, and the other, the device 200 comprising a container 202 with an integrated needle guide 208, if a seal 120, 214 is present covering the proximal opening 122, 216, then the seal 120, 214 is removed. Alternately, the seal 120 covering the proximal opening 122 can be removed before inserting the distal portion 104 of the needle guide 100 over the proximal portion 126 of the container 124. Then, an accessing device 132 comprising a needle 130 at the distal end is provided. Next, an operator inserts the needle 130 through the proximal portion 102, 210 of the needle guide 100, 208 and through the proximal portion 126, 204 of the container 124, 202, thereby accessing the distal storage portion 128, 206 of the container 124, 202. Next, material, such as fluid, is either withdrawn from the container 124, 202 through the needle 134, such as by applying suction proximal to the needle 134, or material, such as fluid, is introduced into the container 124, 202 from the accessing device 132, such as by applying pressure proximal to the needle 134. In a preferred embodiment, the accessing device 132 comprises a syringe 218 with a plunger 220, and applying suction or applying pressure, comprises withdrawing the plunger 220 from the syringe 218 or advancing the plunger 220 into the syringe 218, respectively. Then, the needle 134 is withdrawn from the proximal portion 126, 204 of the container 124, 202 and from the needle guide 100, 208. As will be appreciated by one of ordinary skill in the art with reference to this disclosure, the needle guide 100, 208 helps direct the needle 134, 202 into the container 124, 202 while preventing the needle from slipping and contacting the operator.

If the seal 120, 214 on the proximal opening 122, 216 is resealable, the proximal opening 122, 216 can be resealed. The needle guide 100 can be left in place if there is additional material to be withdrawn from the container 124 or additional material to be introduced into the container 124, or the needle guide 100 can be removed from the container 124 and discarded, or the needle guide 100 can be discarded with the container 124 without removing it from the container 124. In a preferred embodiment, the proximal portion 126, 204 of the container 124, 202 comprises a membrane 136 made of, for example, rubber, and accessing the interior of the container 124, 202 comprises using the needle 134 to pierce the membrane 136.

Figure 13:
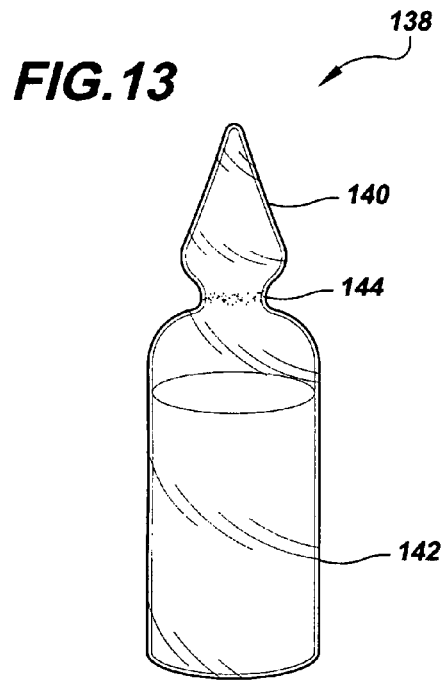
FIG. 13 is a lateral perspective view of a "snap-open" type of medical fluid container.
Figure 14:
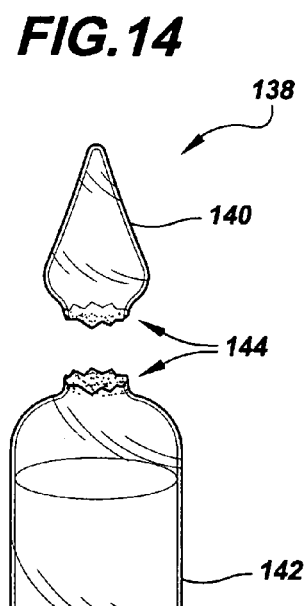
FIG. 14 is a lateral perspective view of the container shown in FIG. 13, which shows the separation of the proximal portion of the container from the distal storage portion of the container along a scored junction.
Figure 15:
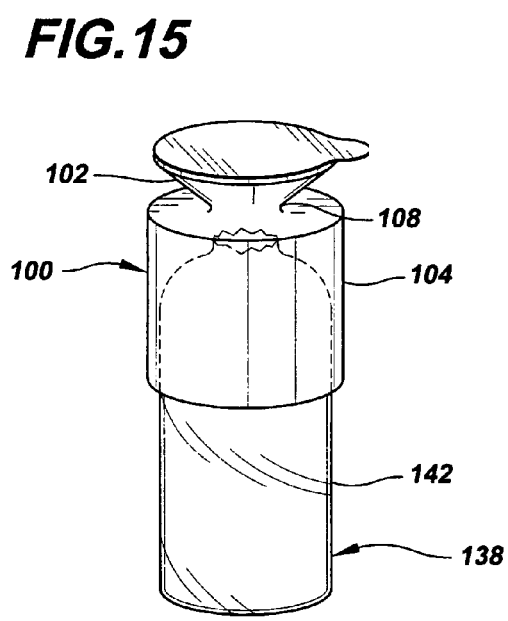
FIG. 15 is a lateral perspective view of the container shown in FIG. 14, after separation of the proximal portion, showing a needle guide according to the present invention inserted over the distal storage portion of the container.

In another preferred embodiment of the method, the container is a "snap-open" type of medical fluid container, such as a glass container. Referring now to FIG. 13 through FIG. 15, there are shown, respectively, a lateral perspective view of a "snap-open" type of medical fluid container (FIG. 13); a lateral perspective view of the container shown in FIG. 13, which shows the separation of the proximal portion of the container from the distal storage portion of the container along a scored junction (FIG. 14); and a lateral perspective view of the container shown in FIG. 14, after separation of the proximal portion, showing a needle guide according to the present invention inserted over the distal storage portion of the container (FIG. 15). As can be seen, the "snap-open" container 138 has a proximal portion 140 and a distal storage portion 142. The proximal portion 140 and the distal storage portion 142 are joined at breakable junction 144 which is preferably scored. In this embodiment of the method, the container 138 is provided along with a needle guide 100. Next, the proximal portion 140 is separated from the distal storage portion 142 by breaking the container 138 at the junction 144 as shown in FIG. 14. Then, the distal portion 104 of the needle guide 100 is inserted over the distal storage portion 142 of the container 138 until the distal end 108 of the proximal portion 102 of the needle guide 100 contacts or comes in close proximity to the distal storage portion 142 of the container 138. Alternately, the needle guide 100 has a proximal portion 102 that is separable from the distal portion 104 as shown in the embodiment in FIG. 5, for example, and the method comprises inserting distal portion 104 of needle guide 100 over the distal storage portion 142 of the container 138 before separating the proximal portion 140 from the distal storage portion 142 by breaking the container 138 at the junction 144. Then, the distal storage portion 142 of the container 138 is separated from the proximal portion 140 by breaking the container 138 at the junction 144, the distal storage portion 142 is removed and discarded and the proximal portion 102 of the needle guide 100 is joined to the distal portion 104 of the needle guide 100. The remainder of the method corresponds to the steps disclosed above with respect to the container 124.

In another embodiment, there is provided a magnetic device for decreasing the incidence of needle injury to an operator who is accessing the interior of a container, such as a medical fluid container, by an accessing device, such as a syringe with a needle attached to the distal end of the syringe. The device has several embodiments.

Referring now to FIG. 16 through FIG. 18, there are shown, respectively, a lateral perspective view of one embodiment of the magnetic device for decreasing the incidence of needle injury to an operator who is accessing the interior of a container, such as a medical fluid container, by an accessing device, such as a syringe with a needle attached to the distal end of the syringe according to the present invention (FIG. 16); another lateral perspective view of the embodiment of the magnetic device shown in FIG. 16 being used to guide a needle from an accessing device into a container retained in the device (FIG. 17); and a top perspective view of the embodiment shown in FIG. 17 taken along line 18—18 (FIG. 18). As can be seen, the device 300 comprises a base 302 comprising a center and a periphery, and comprising a proximal side and a distal side. The device further comprises a plurality of supports 304 attached to the base and extending generally perpendicular to the base 302 and oriented circumferentially around the periphery of the proximal side of the base 302. The base 302 and supports 304 are configured generally to retain the container. In a preferred embodiment, the number and location of the supports 304 are configured to retain a container, such as a medical fluid container, while still allowing the text on the label to be easily read. The base 302 is magnetic and of sufficient strength and configuration to attract a needle approaching the base 302 from proximal to the supports 304 toward the center of the base 302. In a preferred embodiment, the supports 304 comprise springs, or are themselves reversibly deformable allowing the supports 304 to flex toward and away from a line passing perpendicular through the center of the base 302. In this way, a container being placed between the supports 304 will tend to be retained in position. In one embodiment, the base comprises a magnet. In a preferred embodiment, the base 302 is made magnetic through a magnetic field generated by an electromagnet that is activated by electrical power from a power source such as a conventional outlet or battery. In another preferred embodiment, the device 300 comprises sterilizeable materials so that the device 300 can be sterilized and used in a sterile field, such as in a surgical field.

In another embodiment, the present invention is a method of decreasing the incidence of needle injury to an operator who is accessing the interior of a container, such as a medical fluid container, by an accessing device, such as a syringe with a needle attached to the distal end of the syringe. Referring now to FIG. 17 and FIG. 18, the method comprises, first providing a device according to the present invention, such as the magnetic device 300. Next, a container 306 comprising a proximal portion 308 and comprising a distal storage portion 310 to be accessed is provided, and is placed between the supports 304 until the bottom of the container 306 rests near or on the base 302. Then, an accessing device 132 comprising a needle 134 at the distal end is provided. Next, the needle 134 is inserted through the proximal portion 308 of the container 306, thereby accessing the interior of distal storage portion 310 of the container 306. Then, material, such as fluid, is either withdrawn from the container 306 through the needle 134, such as by applying suction proximal to the needle 134, or material, such as fluid, is introduced into the container 306 from the accessing device 132, such as by applying pressure proximal to the needle 134. In a preferred embodiment, the accessing device 132 comprises a syringe 218 with a plunger 220, and applying suction or applying pressure, comprises withdrawing the plunger 220 from the syringe 218 or advancing the plunger 220 into the syringe 218, respectively. Then, the needle 134 is withdrawn from the proximal portion 308 of the container 306. As will be appreciated by one of ordinary skill in the art with reference to this disclosure, the magnetic base 302 attracts the needle 134 approaching the base 302, thereby decreasing the incidence of needle injury to an operator. In another embodiment, the method further comprises withdrawing the needle 134 from the container 306.

Figure 19:
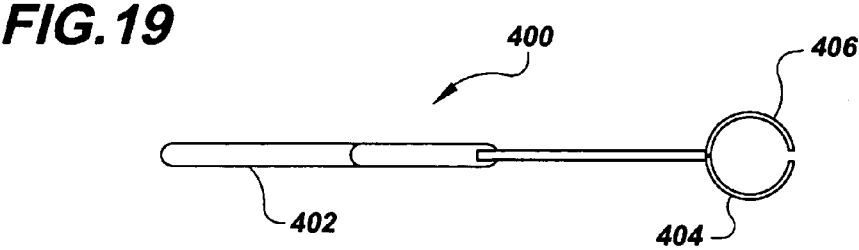
FIG. 19 is a partial top perspective view of another embodiment of the magnetic device according to the present invention.
Figure 20:
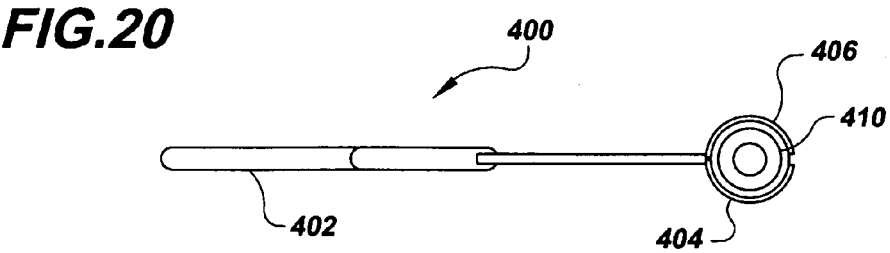
FIG. 20 is another partial top perspective view of the embodiment of the magnetic device shown in FIG. 19 being used to guide a needle from an accessing device into a container retained in the device.
Figure 21:
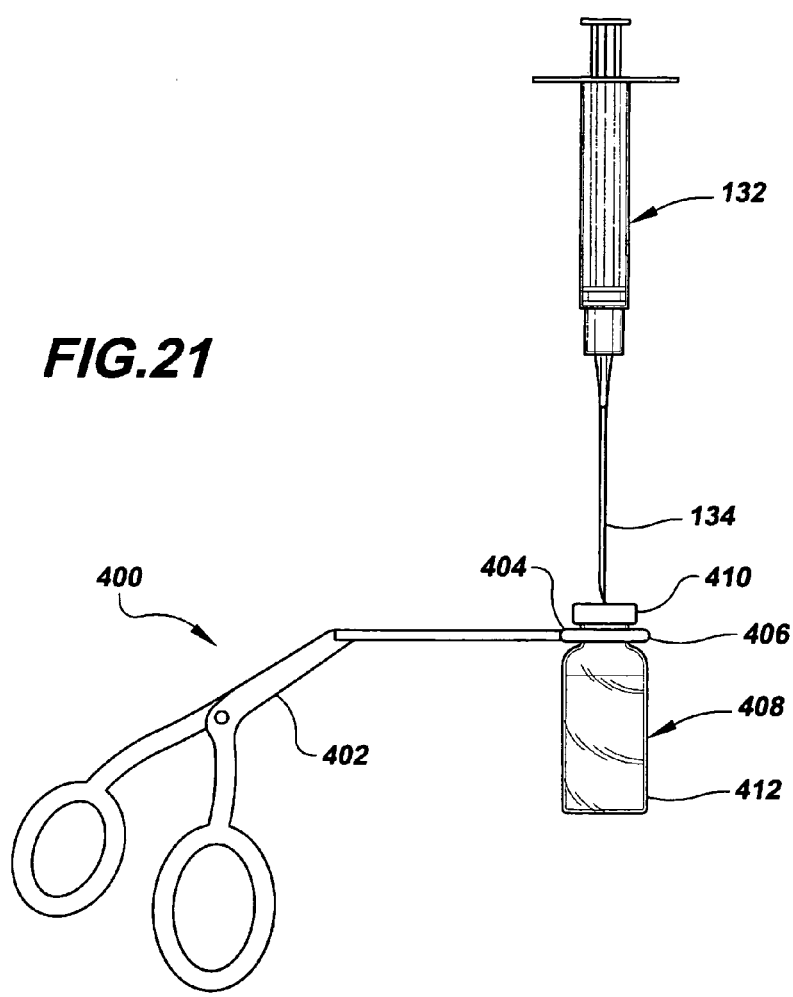
FIG. 21 is a lateral perspective view of the embodiment shown in FIG. 20.

Referring now to FIG. 19 through FIG. 21, there are shown, respectively, a partial top perspective view of another embodiment of the magnetic device for decreasing the incidence of needle injury to an operator who is accessing the interior of a container, such as a medical fluid container, by an accessing device, such as a syringe with a needle attached to the distal end of the syringe according to the present invention (FIG. 19); another partial top perspective view of the embodiment of the magnetic device shown in FIG. 19 being used to guide a needle from an accessing device into a container retained in the device (FIG. 20); and a lateral perspective view of the embodiment shown in FIG. 20 (FIG. 21). As can be seen, the device 400 comprises a proximal actuating portion 402 connected to a distal retaining portion 404. The proximal actuating portion 402 can be any instrument configured to reversibly open and close the distal retaining portion 404. In a preferred embodiment, as shown, the proximal actuating portion 402 comprises medical-style forceps. As will be understood by those with skill in the art with reference to this disclosure, however, the proximal actuating portion 402 can be any instrument that is suitable for the purpose disclosed in this disclosure.

The distal retaining portion 404 comprises a magnet of sufficient strength and configuration to attract a needle approaching the distal retaining portion 404 and to guide the needle toward the center of the distal retaining portion 404. The distal retaining portion 404 is configured to grasp a container, such as a medical fluid container. In one embodiment, the distal retaining portion 404 comprises a plurality of arms 406. The arms 406 can form either an incomplete circular enclosure, as shown, when in the retaining position, or can form a complete circular enclosure when in the retaining position. In another embodiment, the arms 406 comprises a cylinder, either complete or incomplete, when in the retaining position. As will be understood by those with skill in the art with reference to this disclosure, however, the distal retaining portion 404 can be any configuration that is suitable for the purpose disclosed in this disclosure.

In another embodiment, the present invention is a method of decreasing the incidence of needle injury to an operator who is accessing the interior of a container, such as a medical fluid container, by an accessing device, such as a syringe with a needle attached to the distal end of the syringe. Referring now to FIG. 20 and FIG. 21, the method comprises, first, providing a device according to the present invention, such as the magnetic device 400. Next, a container 408 comprising a proximal portion 410 and a distal storage portion 412 to be accessed is provided. Then, the proximal portion 410 of the container 408 is grasped by the distal retaining portion 404 of the device 400, which is actuated by the proximal actuating portion 402. Next, an accessing device 132 comprising a needle 134 at the distal end is provided. Then, the needle 314 is inserted through the proximal portion 410 of the container 408, thereby accessing the interior of distal storage portion 412 of the container 408. The magnetic arms 406 attract the needle 134 approaching the arms 406, thereby decreasing the incidence of needle injury to an operator. In another embodiment, the method further comprises withdrawing material from the container 408 through the needle 134 or introducing material into the container 408 from the accessing device 132. In another embodiment, the method further comprises withdrawing the needle 134 from the container 408. In a preferred embodiment, the method further comprises sterilizing the distal retaining portion 404 prior to actuating the distal retaining portion 404.

Figure 22:
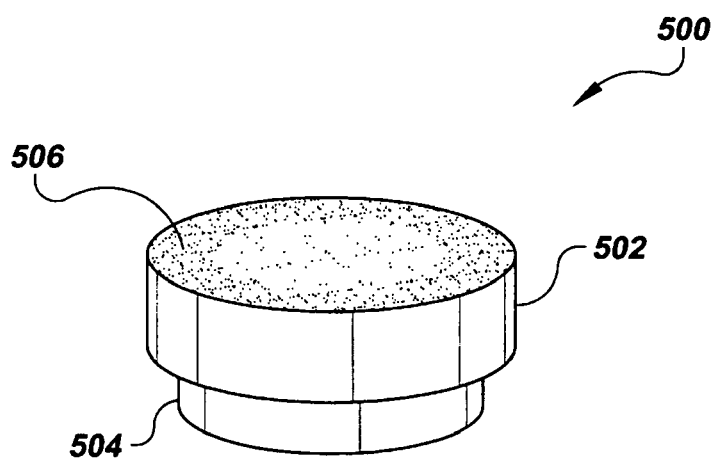
FIG. 22 is a lateral perspective view of another embodiment of the magnetic device according to the present invention.
Figure 23:
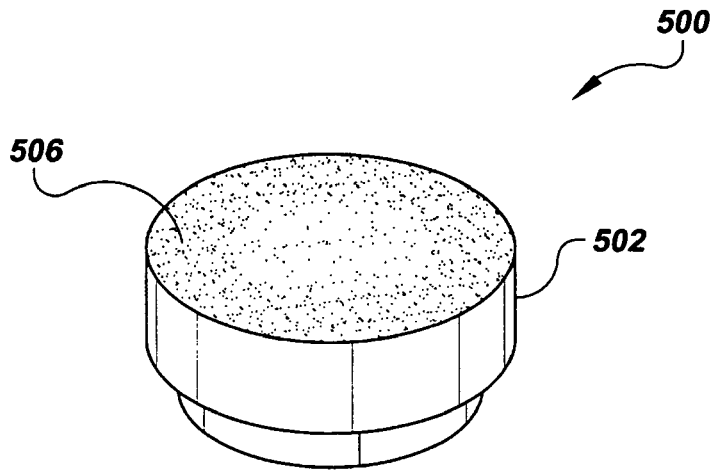
FIG. 23 is a top perspective view of the embodiment of the magnetic device shown in FIG. 22.

Referring now to FIG. 22 and FIG. 23, there are shown, respectively, a lateral perspective view of another embodiment of the magnetic device for decreasing the incidence of needle injury to an operator who is accessing the interior of a container, such as a medical fluid container, by an accessing device, such as a syringe with a needle attached to the distal end of the syringe according to the present invention (FIG. 22) and a top perspective view of the embodiment of the magnetic device shown in FIG. 22 (FIG. 23). As can be seen, the device 500 comprises a proximal portion 502, and comprises a distal portion 504 attached to the proximal portion. The proximal portion comprises domain-sized, uncoated magnetic particles 506, generally indicated by the crosshatching, in a configuration more dense around the periphery and less dense in the center, thereby creating a circular magnet with a center that is substantially free of magnetic particles 506. In one embodiment, separate magnetic particles are embedded directly into the material of the proximal portion 504 by mixing the magnetic particles into uncast rubber, and casting the device 500 to draw the magnetic particles toward the periphery according to techniques known to those with skill in the art. The distal portion can also comprise magnetic particles 506 in the periphery. In another embodiment, the proximal portion 502 comprises a washer with the magnetic particles 506 embedded into the washer, and where the washer is then attached to or embedded directly in the proximal portion 502. In a preferred embodiment, the washer is sealed in a resin. The distal portion 504 is configured to fit snugly into the proximal opening of a container.

In another embodiment, the present invention is a method of decreasing the incidence of needle injury to an operator who is accessing the interior of a container, such as a medical fluid container, by an accessing device, such as a syringe with a needle attached to the distal end of the syringe. The method comprises, first, providing a device according to the present invention, such as the magnetic device 500. Next, the distal portion 504 of the device 500 is introduced into the proximal portion of a container, such as a medical fluid container, thereby substantially sealing the proximal portion of the container. Then, an accessing device comprising a needle at the distal end is provided. Next, the needle is inserted through the proximal portion of the device and into the container. Then, material, such as fluid, is either withdrawn from the container through the needle, such as by applying suction proximal to the needle, or material, such as fluid, is introduced into the container from the accessing device, such as by applying pressure proximal to the needle. In a preferred embodiment, the accessing device comprises a syringe with a plunger, and applying suction or applying pressure, comprises withdrawing the plunger from the syringe or advancing the plunger into the syringe, respectively. Then, the needle is withdrawn from the container and from the proximal portion 502 of the device 500. As will be appreciated by one of ordinary skill in the art with reference to this disclosure, the magnetic particles 506 direct the needle toward the center of the device 500, thereby decreasing the incidence of needle injury to an operator.

Figures 24, 25:
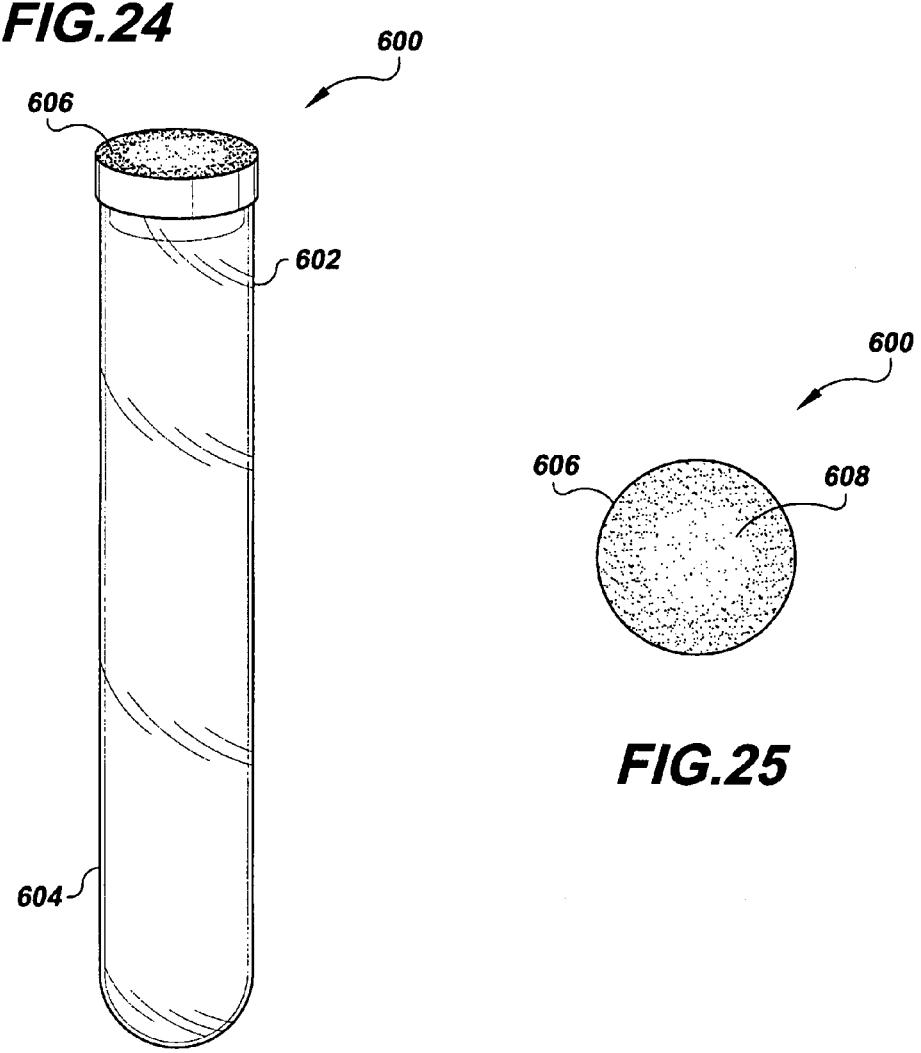
FIG. 24 is a lateral perspective view of another embodiment of the magnetic device according to the present invention.
FIG. 25 is a top perspective view of the embodiment of the magnetic device shown in FIG. 24.

Referring now to FIG. 24 and FIG. 25, there are shown, respectively, a lateral perspective view of another embodiment of the magnetic device for decreasing the incidence of needle injury to an operator who is accessing the interior of a container, such as a medical fluid container, by an accessing device, such as a syringe with a needle attached to the distal end of the syringe according to the present invention (FIG. 24) and a top perspective view of the embodiment of the magnetic device shown in FIG. 24 (FIG. 25). As can be seen, the device 600 is a container, such as a medical fluid container, comprising a proximal portion 602 and a distal storage portion 604. The device 600 further comprises a needle guide 606, integrally attached to the proximal portion 602 of the device 600. The needle guide 606 comprises a membrane or stopper sealing the proximal portion 602 of the device 600. The needle guide 606 comprises domain-sized, uncoated magnetic particles 608, generally indicated by the crosshatching, in a configuration more dense around the periphery and less dense in the center, thereby creating a circular magnet with a center that is substantially free of magnetic particles 608. In one embodiment, separate magnetic particles 608 are embedded directly into the material of the membrane or stopper by mixing the magnetic particles 608 into uncast rubber, and casting the membrane or stopper to draw the magnetic particles 608 toward the periphery according to techniques known to those with skill in the art. In one embodiment, a seal is used to cover the needle guide 606 prior to use to maintain sterility of the needle guide 606 before use. In another embodiment, the seal covers the entire device 600. In another embodiment, the seal is resealable.

In another embodiment, the present invention is a method of decreasing the incidence of needle injury to an operator who is accessing the interior of a container, such as a medical fluid container, by an accessing device, such as a syringe with a needle attached to the distal end of the syringe. The method comprises, first, providing a device according to the present invention, such as the magnetic device 600. If a seal is present covering the needle guide 606, then the seal is removed. Then, an accessing device comprising a needle at the distal end is provided. Next, an operator inserts the needle through the needle guide 606 in the proximal portion 602 of the device 600, thereby accessing the distal portion 604 of the device 600. Next, material, such as fluid, is either withdrawn from the device 600 through the needle, such as by applying suction proximal to the needle, or material, such as fluid, is introduced into the device 600 from the accessing device, such as by applying pressure proximal to the needle. In a preferred embodiment, the accessing device comprises a syringe with a plunger, and applying suction or applying pressure, comprises withdrawing the plunger from the syringe or advancing the plunger into the syringe, respectively. Then, the needle is withdrawn from the proximal portion 602 of the device 600 and from the needle guide 606. As will be appreciated by one of ordinary skill in the art with reference to this disclosure, the magnetic particles 606 direct the needle toward the center of the device 600, thereby decreasing the incidence of needle injury to an operator.

In another embodiment of the present invention, the seal on either the proximal opening or on the distal opening or both, or the seal covering the entire device comprises a first layer and a second layer, and further comprises a sterilizing pad such as an alcohol pad between the first layer and the second layer. Additionally, the methods of the present invention, can further comprise removing the first layer of the seal to access the sterilizing pad, and then using the sterilizing pad to sterilize part of the container to be contacted with the needle from the accessing device.

Although the present invention has been discussed in considerable detail with reference to certain preferred embodiments, other embodiments are possible. For example, in one embodiment, the present invention is a combination of one or more than one needle guide or one or more than one device for decreasing the incidence of needle injury according to the present invention. Therefore, the scope of the appended claims should not be limited to the description of preferred embodiments contained in this disclosure. All references cited herein are incorporated by reference to their entirety.

What is claimed is:

1. A needle guide for decreasing the incidence of needle injury to an operator who is accessing the interior of a container, such as a medical fluid container, by an accessing device, such as a syringe with a needle attached to the distal end of the syringe, the needle guide comprising:
   a proximal portion comprising a proximal end that is at least partly open and comprising a distal end; and
   a distal portion connected to the proximal portion, the distal portion comprising a proximal end and comprising a distal end that is at least partly open;
   where the proximal portion comprises an inner surface that tapers from the proximal end of the proximal portion to the distal end of the proximal portion;
   where the distal portion comprises an inner surface that is continuous with the inner surface of the proximal portion though an opening; and
   where the distal portion is configured such that the inner surface of the distal portion fits snugly over part or all of the container to be accessed.

2. The needle guide of claim 1, where the proximal portion has a substantially conical shape with the larger end proximally and the narrow end distally.

3. The needle guide of claim 1 further comprising one or more than one seal, sealing the proximal end of the proximal portion and sealing the distal end of the distal portion of the needle guide to maintain sterility of the inner surface of the proximal portion and the inner surface of the distal portion of the needle guide prior to use.

4. The needle guide of claim 3, where the seal is a metal foil removably attached to the lip of the proximal portion by an adhesive.

5. The needle guide of claim 3, where the seal is a wrapping covering the entire needle guide.

6. The needle guide of claim 3, where the seal is resealable.

7. The needle guide of claim 3, where the seal comprises a first layer and a second layer, and further comprises a sterilizing pad between the first layer and the second layer.

8. The needle guide of claim 1, where the proximal portion and the distal portion of the needle guide are configured to be separable from one another by the operator.

9. The needle guide of claim 8, where the distal end of the proximal portion comprises a mechanism that mates with a companion mechanism on the proximal end of the distal portion device.

10. The needle guide of claim 9, where the mechanism on the proximal portion and the mechanism on the distal portion are interlocking screw-type mechanisms.

11. A device for decreasing the incidence of needle injury to an operator who is accessing the interior of the container by an accessing device, the device comprising:
    a container comprising a proximal portion and a distal storage portion; and
    a needle guide comprising a proximal portion with a proximal end and a distal end, and comprising a distal portion, where the distal portion of the needle guide is integrally attached to the proximal portion of container; and
    where the proximal portion of the needle guide tapers from the proximal end to the distal end.

12. The device of claim 11, where the proximal portion of the needle guide has a substantially conical shape with the larger end proximally and the narrow end distally.

13. The device of claim 11, where the proximal portion of the needle guide has an inner surface, and further comprising a seal, sealing the proximal end of the proximal portion of the needle guide to maintain sterility of the inner surface of the proximal portion prior to use.

14. The device of claim 13, where the seal is a metal foil removably attached to the lip of the proximal portion of the needle guide by an adhesive.

15. The device of claim 13, where the seal is a wrapping covering the entire device.

16. The device of claim 13, where the seal is resealable.

17. The device of claim 13, where the seal comprises a first layer and a second layer, and further comprises a sterilizing pad between the first layer and the second layer.

18. A method of decreasing the incidence of needle injury to an operator who is accessing the interior of a container by an accessing device, the method comprising:
    a) providing a container comprising a proximal portion and comprising a distal storage portion whose interior is to be accessed, and providing a needle guide according to claim 1;
    b) inserting the distal portion of the needle guide over the proximal portion of the container until that the distal end of the proximal portion of the needle guide contacts or comes in close proximity to the proximal portion of the container;

c) providing an accessing device comprising a needle at the distal end; and d) inserting the needle through the proximal portion of the needle guide and through the proximal portion of the container, thereby accessing the distal storage portion of the container.

19. The method of claim 18, where the proximal portion of the container comprises a seal, and where the method further comprises removing the seal.

20. The method of claim 18, where the distal end of the distal portion of the needle guide comprises a seal, and where the method further comprises removing the seal.

21. The method of claim 18, where the proximal end of the proximal portion of the needle guide comprises a seal, and where the method further comprises removing the seal.

22. The method of claim 21, further comprising resealing the proximal end of the proximal portion of the needle guide.

23. The device of claim 21, where the seal comprises a first layer and a second layer, and further comprises a sterilizing pad between the first layer and the second layer, and where the method further comprises removing the first layer of the seal to access the sterilizing pad, and then using the sterilizing pad to sterilize part of the container to be contacted with the needle from the accessing device.

24. The method of claim 18, further comprising withdrawing material from the container through the needle or introducing material into the container from the accessing device.

25. The method of claim 18, further comprising withdrawing the needle from the proximal portion of the container, and from the needle guide.

26. The method of claim 18, where the container is a "snap-open" type of medical fluid container comprising a breakable junction between the proximal portion and the distal storage portion; and where the method further comprises separating the proximal portion of the container from the distal storage portion of the container by breaking the container at the junction.

27. The method of claim 18, where the container is a "snap-open" type of medical fluid container comprising a breakable junction between the proximal portion and the distal storage portion;

where the proximal portion and the distal portion of the needle guide are configured to be separable from one another by the operator; and where the method further comprises inserting distal portion of needle guide over the distal storage portion of the container before separating the proximal portion from the distal storage portion by breaking the container at the junction, separating the distal storage portion of the container from the proximal portion by breaking the container at the junction, removing the distal storage portion, and then joining the proximal portion of the needle guide to the distal portion of the needle guide.

28. A method of decreasing the incidence of needle injury to an operator who is accessing the interior of a container, such as a medical fluid container, by an accessing device, such as a syringe with a needle attached to the distal end of the syringe, the method comprising:

a) providing a device according to claim 11;

b) providing an accessing device comprising a needle at the distal end; and c) inserting the needle through the proximal portion of the needle guide and through the proximal portion of the container, thereby accessing the distal storage portion of the container.

29. The method of claim 28, where the proximal end of the proximal portion of the needle guide comprises a seal, and where the method further comprises removing the seal.

30. The method of claim 29, further comprising resealing the proximal end of the proximal portion of the needle guide.

31. The method of claim 28, further comprising withdrawing material from the container through the needle or introducing material into the container from the accessing device.

32. The method of claim 28, further comprising withdrawing the needle from the proximal portion of the container and from the needle guide.

33. A device for decreasing the incidence of needle injury to an operator who is accessing the interior of the container by an accessing device, such as a syringe with a needle attached to the distal end of the syringe, the device comprising:

a base comprising a center and a periphery, and comprising a proximal side and a distal side; and a plurality of supports attached to the base extending generally perpendicular to the base and oriented circumferentially around the periphery of the proximal side of the base;

where the base and supports are configured generally to retain the container; and where the base is magnetic and of sufficient strength and configuration to attract a needle approaching the base from proximal to the supports toward the center of the base.

34. A method of decreasing the incidence of needle injury to an operator who is accessing the interior of a container comprising a proximal portion and a distal storage portion to be accessed, by an accessing device comprising a needle at the distal end, the method comprising:

a) providing a device according to claim 33;

b) placing the container between the supports;

c) providing the accessing device; and d) inserting the needle through the proximal portion of the container, thereby accessing the distal storage portion of the container.

35. The method of claim 34, further comprising withdrawing material from the container through the needle or introducing material into the container from the accessing device.

36. The method of claim 34, further comprising withdrawing the needle from the proximal portion of the container.

37. A device for decreasing the incidence of needle injury to an operator who is accessing the interior of the container by an accessing device, such as a syringe with a needle attached to the distal end of the syringe, the device comprising:

a proximal actuating portion; and a distal retaining portion connected to the proximal actuating portion;

where the proximal actuating portion is configured to reversibly open and close the distal retaining portion;

where the distal retaining portion comprises a magnet of sufficient strength and configuration to attract a needle approaching the distal retaining portion and to guide the needle toward the center of the distal retaining portion; and where the distal retaining portion is configured to grasp the container.

38. The device of claim 37, where the distal retaining portion comprises a plurality of arms.

39. The device of claim 38, where the arms form an incomplete circular enclosure.

40. The device of claim 38, where the arms form a cylinder.

41. A method of decreasing the incidence of needle injury to an operator who is accessing the interior of a container comprising a proximal portion and a distal storage portion to be accessed, by an accessing device comprising a needle at the distal end, the method comprising:
   a) providing a device according to claim 37;
   b) providing the container to be accessed;
   c) actuating the distal retaining portion to grasp the proximal portion of the container with the distal retaining portion;
   d) providing the accessing device; and
   e) inserting the needle through the proximal portion of the container, thereby accessing the distal storage portion of the container.

42. The method of claim 41, further comprising withdrawing material from the container through the needle or introducing material into the container from the accessing device.

43. The method of claim 41, further comprising withdrawing the needle from the proximal portion of the container.

44. The method of claim 41, further comprising sterilizing the distal retaining portion prior to actuating the distal retaining portion.

45. A device for decreasing the incidence of needle injury to an operator who is accessing the interior of the container by an accessing device, the device comprising:
   a proximal portion comprising a center and a periphery; and
   a distal portion attached to the proximal portion, and comprising a center and a periphery;
   where the proximal portion comprises magnetic particles in a configuration more dense around the periphery and less dense in the center; and
   where the distal portion is configured to fit snugly into the proximal opening of the container.

46. The device of claim 45, where the distal portion comprises magnetic particles in a configuration more dense around the periphery and less dense in the center.

47. The device of claim 45, where the magnetic particles are embedded directly into the proximal portion.

48. The device of claim 45, where the proximal portion comprises a washer with the magnetic particles embedded into the washer, and where the washer is attached to or embedded directly in the proximal portion.

49. A method of decreasing the incidence of needle injury to an operator who is accessing the interior of a container comprising a proximal portion and a distal storage portion to be accessed, by an accessing device comprising a needle at the distal end, the method comprising:
   a) providing a device according to claim 45;
   b) providing the container to be accessed;
   c) introducing the distal portion of the device into the proximal portion of the container, thereby substantially sealing the proximal portion of the container;
   d) providing the accessing device; and
   e) inserting the needle through the proximal portion of the device and into the container.

50. The method of claim 49, further comprising withdrawing material from the container through the needle or introducing material into the container from the accessing device.

51. The method of claim 49, further comprising withdrawing the needle from the proximal portion of the container.

52. A device for decreasing the incidence of needle injury to an operator who is accessing the interior of the container by an accessing device, the device comprising:
   a proximal portion and a distal storage portion attached to the proximal portion; and
   a needle guide comprising a center and a periphery;
   where the needle guide is integrally attached to the proximal portion and seals the proximal portion of the device; and
   where the needle guide comprises magnetic particles in a configuration more dense around the periphery and less dense in the center.

53. The device of claim 52, further comprising a seal covering the needle guide to maintain sterility of the needle guide before use.

54. A method of decreasing the incidence of needle injury to an operator who is accessing the interior of a device comprising a proximal portion and a distal storage portion to be accessed, by an accessing device comprising a needle at the distal end, the method comprising:
   a) providing a device according to claim 52;
   b) providing the accessing device; and
   c) inserting the needle through the needle guide of the device, thereby accessing the distal storage portion.

55. The method of claim of claim 54, where the device provided further comprises a seal covering the needle guide to maintain sterility of the needle guide before use, and where the method further comprises removing the seal.

56. The method of claim 54, further comprising withdrawing material from the device through the needle or introducing material into the device from the accessing device.

57. The method of claim 54, further comprising withdrawing the needle from the device.

* * * * *